United States Patent [19]

Mack et al.

[11] Patent Number: Plant 6,644

[45] Date of Patent: Feb. 28, 1989

[54] CHRYSANTHEMUM PLANT NAMED ILLUSION

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 99,741

[22] Filed: Sep. 22, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Illusion particularly characterized by its flat capitulum form; spoon daisy capitulum type; white ray floret color; diameter across face of capitulum of up to 8.5 cm at maturity; short plant height with spreading and prolific branching pattern; average natural season flower date of August 29 in Salinas, Calif. and September 25 in Hightstown, N.J.; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of Chrysanthemum, botanically known as *Chrysanthemum morifolium,* Ramat., and referred to by the cultivar name Illusion.

Illusion, identified as 84M23004, was originated from a cross made by Grace H. Mack in a controlled breeding program in New Canaan, Conn., in 1983.

The parents of Illusion were both unnamed seedlings.

Illusion was discovered and selected as one flowering plant within the progeny of the stated cross by Cornelis P. VandenBerg in September of 1984, in a controlled environment in Salinas, Calif.

The first act of asexual reproduction of Illusion was accomplished when vegetative cuttings were taken from the initial selection in November of 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Illusion are firmly fixed and are retained through successive generations of asexual reproduction.

Illusion has not been observed under all possible environmental conditions. The phenotype may vary significantly with variations in environment such as temperature, light intensity, and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Illusion, which, in combination, distinguish this Chrysanthemum as a new and distinct cultivar:

1. Flat capitulum form.
2. Spoon daisy capitulum type.
3. White ray floret color.
4. Diameter across face of capitulum up to 8.5 cm at maturity.
5. Short plant height.

6. Spreading and prolific branching pattern.
7. Average natural season flower date of August 29 in Salinas, Calif., and September 25 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Illusion, with the colors being as nearly true as possible with illustrations of this type.

Sheet 1 is a color photograph of Illusion grown as a pinched spray pot mum.

Sheet 2 is a black and white photograph of three views of the inflorescence of Illusion.

Sheet 3 is a black and white photograph showing the upper and under sides of the leaves of Illusion at three stages of development (mature, intermediate and immature).

Of the commercial cultivars known to the inventors, the most similar in comparison to Illusion is Ballerina, disclosed in U.S. Plant Pat. No. 5,440. Reference is made to attached Chart A, which compares certain characteristics of Illusion to the same characteristics of Ballerina.

Similar traits are ray floret color, diameter across face of capitulum, and controlled flowering response. Illusion is a flat spoon daisy. Ballerina is a spider decorative. Illusion has a more spreading and prolific branching pattern, a shorter plant height, and an earlier natural season flowering response than Ballerina.

In the following description, color references are made to the Royal Horticultural Society Colour Chart. The color values were determined on plant material grown under controlled greenhouse conditions in Salinas, Calif. on May 29, 1987.

Classification:

*Botanical.*—*Chrysanthemum morifolium,* Ramat., cv. Illusion.

*Commercial.*—Spoon daisy spray pot mum and garden mum.

INFLORESCENCE

A. Capitulum:

*Form.*—Flat.

*Type.*—Spoon daisy.

*Diameter across face.*—Up to 8.5 cm at maturity.

B. Corolla of ray florets:

*Color (general tonality from a distance of three meters).*—White.

*Color (upper surface, spoon tips).*—White.

*Color (under surface, tubes).*—155A, maturing to 155D.

*Shape.*—Tubular, with slight spoon tip.

C. Corolla of disc florets:

*Color (mature).*—13B to 14B.

*Color (immature).*—151C to 151D.

D. Reproductive organs:

*Androecium.*—Present on disc florets only; moderate pollen.

*Gynoecium.*—Present on both ray and disc florets.

PLANT

A. General appearance:

*Height.*—Short.

*Branching pattern.*—Spreading and prolific.

B. Foliage:

*Color (upper surface).*—137B.

*Color (under surface).*—147B.

*Shape.*—Lobed and slightly serrated.

CHART A

Comparison of Illusion and Ballerina

| | RAY FLORET | CAPITULUM | BRANCHING |
|---|---|---|---|

CHART A-continued

Comparison of Illusion and Ballerina

| CULTIVAR | COLOR | FORM & TYPE | PATTERN |
|---|---|---|---|
| Illusion | White | Flat<br>Spoon<br>Daisy | Spreading<br>and prolific |
| Ballerina | White | Spider<br>Decorative | Upright |

| CULTIVAR | DIAMETER ACROSS FACE OF CAPITULUM | CONTROLLED PLANT HEIGHT | FLOWERING RESPONSE |
|---|---|---|---|
| Illusion | Up to 8.5 cm | Short | 7 weeks |
| Ballerina | Up to 8.5 cm | Medium | 7 weeks |

| CULTIVAR | AVERAGE NATURAL SEASON SALINAS | FLOWER DATE HIGHTSTOWN |
|---|---|---|
| Illusion | Aug. 29 | Sept. 25 |
| Ballerina | Sept. 3 | Sept. 28 |

COMPARISONS MADE OF PLANTS GROWN UNDER NATURAL SEASON OUTSIDE CONDITIONS IN SALINAS, CALIFORNIA AND IN HIGHTSTOWN, NEW JERSEY

We claim:

1. A new and distinct Chrysanthemum plant named Illusion, as described and illustrated, and particularly characterized as to uniqueness by the combined characteristics of flat capitulum form; spoon daisy capitulum type; white ray floret color; diameter across face of capitulum of up to 8.5 cm at maturity; short plant height with spreading and prolific branching pattern; average natural season flower date of August 29 in Salinas, Calif. and September 25 in Hightstown, N.J.; uniform seven week photoperiodic flowering response to short days in photoperiodic controlled flowering programs; and durable, uniform performance in outside fall flowerings and in spring small pot flowering programs.

* * * * *

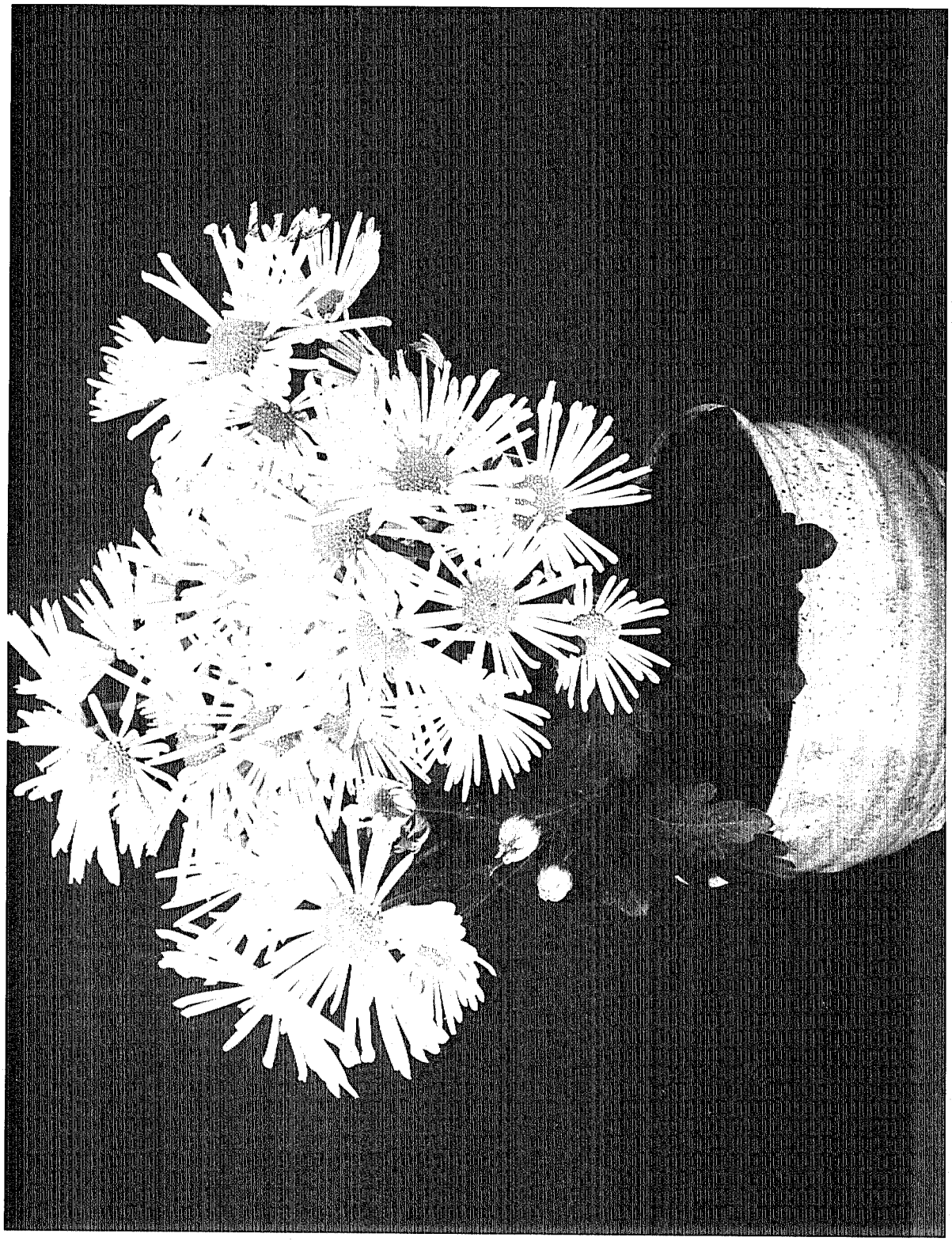

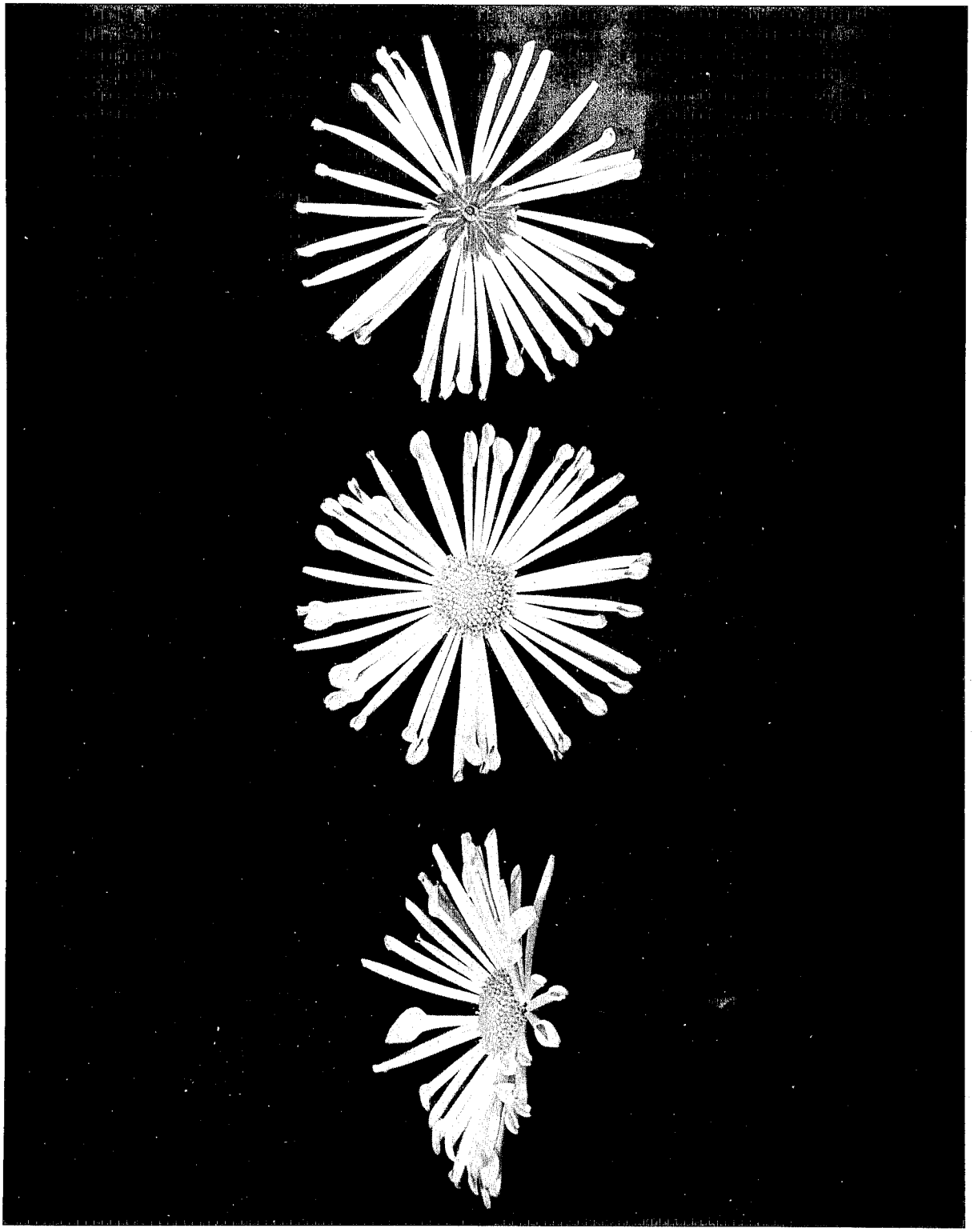

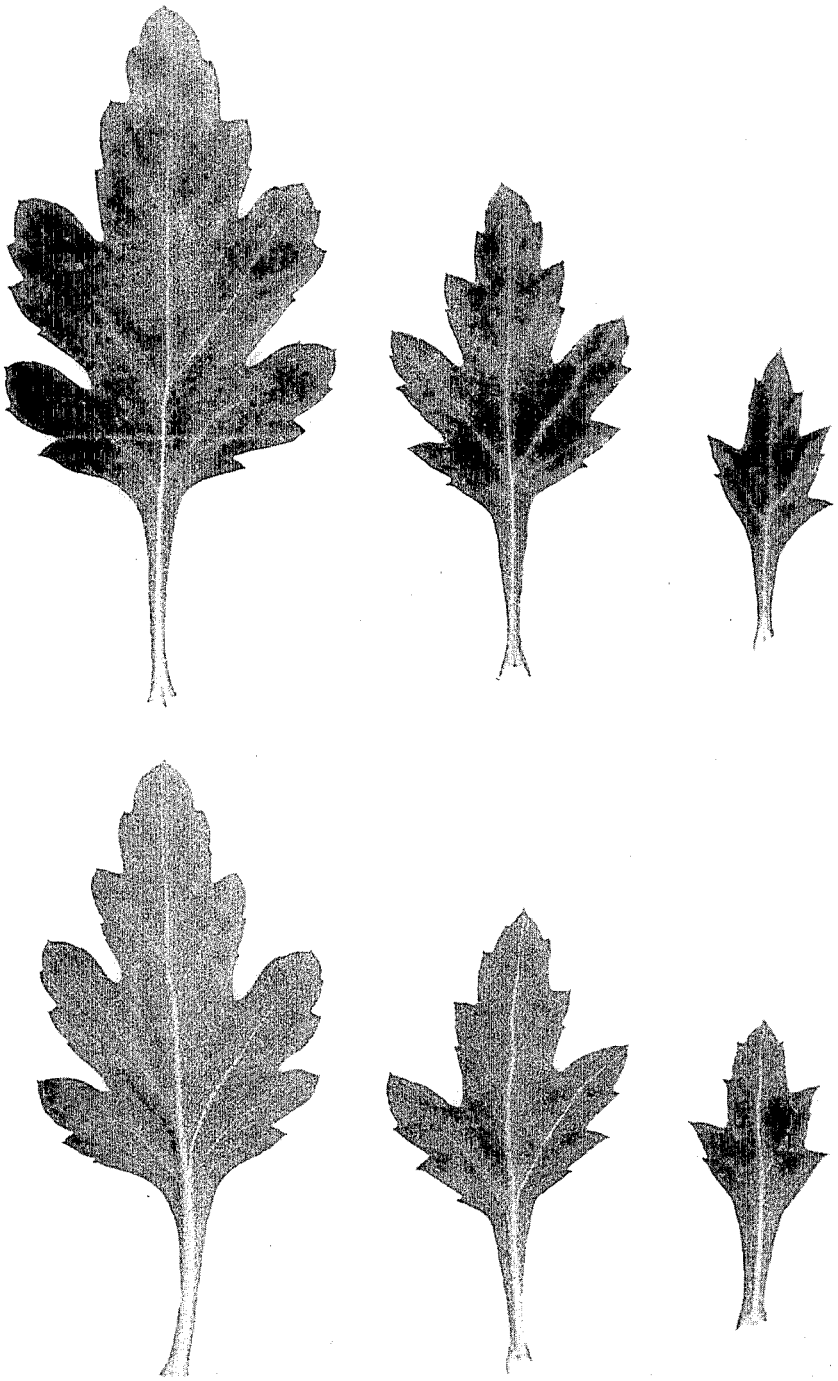

UNITED STATES PATENT AND TRADEMARK OFFICE

CERTIFICATE OF CORRECTION

PATENT NO. : PP 6,644

DATED : February 28, 1989

INVENTOR(S) : Grace H. Mack and Cornelis P. VandenBerg

It is certified that error appears in the above—identified patent and that said Letters Patent is hereby corrected as shown below:

Columns 3 and 4, Chart A, should appear as shown below:

CHART A

Comparison of Illusion and Ballerina

| CULTIVAR | RAY FLORET COLOR | CAPITULUM FORM & TYPE | BRANCHING PATTERN |
|---|---|---|---|
| Illusion | White | Flat Spoon Daisy | Spreading and prolific |
| Ballerina | White | Spider Decorative | Upright |

| | DIAMETER ACROSS FACE OF CAPITULUM | PLANT HEIGHT | CONTROLLED FLOWERING RESPONSE |
|---|---|---|---|
| Illusion | Up to 8.5 cm | Short | 7 weeks |
| Ballerina | Up to 8.5 cm | Medium | 7 weeks |

AVERAGE NATURAL SEASON FLOWER DATE

| | SALINAS | HIGHTSTOWN |
|---|---|---|
| Illusion | Aug. 29 | Sept. 25 |
| Ballerina | Sept. 3 | Sept. 28 |

UNITED STATES PATENT AND TRADEMARK OFFICE

CERTIFICATE OF CORRECTION

PATENT NO. : PP 6,644

DATED : February 28, 1989

INVENTOR(S) : Grace H. Mack and Cornelis P. VandenBerg

It is certified that error appears in the above—identified patent and that said Letters Patent is hereby corrected as shown below:

COMPARISONS MADE OF PLANTS GROWN UNDER
NATURAL SEASON OUTSIDE CONDITIONS
IN SALINAS, CALIFORNIA AND IN HIGHTSTOWN, NEW JERSEY

Signed and Sealed this

Twenty-sixth Day of June, 1990

*Attest:*

HARRY F. MANBECK, JR.

*Attesting Officer*

*Commissioner of Patents and Trademarks*